(12) United States Patent
Kelp

(10) Patent No.: US 11,504,227 B2
(45) Date of Patent: Nov. 22, 2022

(54) INJECTOR ASSEMBLY FOR INSERTING AN INTRAOCULAR LENS

(71) Applicant: Carl Zeiss Meditec AG, Jena (DE)

(72) Inventor: Martin Kelp, Berlin (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 17/615,887

(22) PCT Filed: Jun. 4, 2020

(86) PCT No.: PCT/EP2020/065512
§ 371 (c)(1),
(2) Date: Dec. 2, 2021

(87) PCT Pub. No.: WO2020/245289
PCT Pub. Date: Dec. 10, 2020

(65) Prior Publication Data
US 2022/0265420 A1    Aug. 25, 2022

(30) Foreign Application Priority Data
Jun. 5, 2019   (DE) .................... 10 2019 115 125.2

(51) Int. Cl.
*A61F 2/16* (2006.01)
(52) U.S. Cl.
CPC .................. *A61F 2/1667* (2013.01)
(58) Field of Classification Search
CPC .... A61F 2/1662; A61F 2/1664; A61F 2/1667; A61F 2/167; A61F 2/1672; A61F 2/1675;
(Continued)

(56) References Cited

U.S. PATENT DOCUMENTS

| 2012/0022548 A1* | 1/2012 | Zacharias | A61F 2/1672 |
| | | | 606/107 |
| 2013/0096589 A1* | 4/2013 | Spencer | A61B 17/320758 |
| | | | 606/159 |
| 2015/0342726 A1* | 12/2015 | Deacon | A61F 2/1664 |
| | | | 623/4.1 |

FOREIGN PATENT DOCUMENTS

| EP | 0302278 A1 | 2/1989 |
| EP | 0830083 A1 | 3/1998 |
| WO | WO-96/37152 A1 | 11/1996 |

OTHER PUBLICATIONS

Written Opinion of the International Searching Authority for PCT/EP2020/065512 (ISA/CN) dated Sep. 10, 2020 (4 pages).
(Continued)

*Primary Examiner* — Kathleen S Holwerda
(74) *Attorney, Agent, or Firm* — Alston & Bird LLP

(57) ABSTRACT

Provided is an injector assembly, comprising: —an injector, which has a plunger and a cannula and is designed to move an intraocular lens through the cannula by means of a translational motion of the plunger; —a magnetic coupling; and—a drive unit, which has a first coupling half of the magnetic coupling, a motor, which is designed to drive the first coupling half into a first rotational motion, and a housing, within which the first coupling half and the motor are encapsulated and which has an annular housing portion, which delimits a channel having a circular cross-section. The injector has a second coupling half of the magnetic coupling, and the injector and the second coupling half are arranged in the channel. The first coupling half is arranged around the annular housing portion and is thus designed to perform the first rotational motion around the annular housing portion and thus to drive the second coupling half into a second rotational motion by means of a magnetic field of the magnetic coupling, which magnetic field penetrates the
(Continued)

annular housing portion. The injector is designed to convert the second rotational motion into the translational motion of the plunger.

10 Claims, 2 Drawing Sheets

(58) Field of Classification Search
CPC ......... A61F 2/1678; A61B 2017/00017; A61B 2017/00039; A61B 2017/00075
See application file for complete search history.

(56) References Cited

OTHER PUBLICATIONS

German Office Action for German Patent Application No. 10 2019 115 125.2, dated Mar. 6, 2020, (9 pages), German Patent Office, Munich, Germany.
International Search Report and Written Opinion for International Application No. PCT/EP2020/065512, dated Sep. 10, 2020, (11 pages), European Patent Office, Rijswijk, Netherlands.

\* cited by examiner

INJECTOR ASSEMBLY FOR INSERTING AN INTRAOCULAR LENS

CROSS-REFERENCE TO RELATED APPLICATIONS

The present application is a national phase entry of International Application No. PCT/EP2020/065512, filed Jun. 4, 2020, which claims priority to German Patent Application No. 10 2019 115 125.2, filed Jun. 5, 2019, which are incorporated herein by reference in their entireties.

The invention relates to an injector assembly for inserting an intraocular lens into the capsular bag of an eye.

In cataract treatment of an eye, only a small incision is usually made in the cornea of the eye, said incision being large enough to allow a cannula to be inserted through the incision into the eye. After the incision has been made in the cornea, the lens of the eye is broken up by phacoemulsification and then aspirated from the capsular bag of an eye. An intraocular lens is then inserted into the eye. In doing this, the intraocular lens is folded, such that it fits through the cannula of an injector. The cannula is inserted into the capsular bag through the incision, and the folded intraocular lens is pushed by the injector through the cannula into the capsular bag, in which the intraocular lens unfolds and thus replaces the original lens.

A plunger of the injector can be pressed by hand by a doctor performing the treatment, or the doctor can use a drive unit with a motor by means of which the plunger is moved. It is disadvantageous that conventional drive units can be sterilized only in a complex or inadequate manner. This means that the drive units can be used only once and then have to be disposed of.

The object of the invention is therefore to provide an injector assembly with an injector and a drive unit, wherein the drive unit can be sterilized easily.

The injector assembly according to the invention has an injector, which has a plunger and a cannula and is configured to move an intraocular lens through the cannula by means of a translational movement of the plunger, a magnetic coupling and a drive unit, which has a first coupling half of the magnetic coupling, a motor, which is configured to drive the first coupling half into a first rotational movement, and a housing, within which the first coupling half and the motor are encapsulated and which has an annular housing portion which delimits a channel which has a circular cross section, wherein the injector has a second coupling half of the magnetic coupling, and the injector and the second coupling half are arranged in the channel, wherein the first coupling half is arranged around the annular housing portion and is thus configured to carry out the first rotational movement around the annular housing portion and therefore to drive the second coupling half into a second rotational movement by means of a magnetic field of the magnetic coupling penetrating the annular housing portion, wherein the injector is configured to convert the second rotational movement into the translational movement of the plunger.

By providing the magnetic coupling and its magnetic field penetrating the annular housing portion, it is possible to encapsulate the housing. The drive unit with the encapsulated housing can easily be sterilized, for example by exposing the drive unit to an elevated temperature and an increased pressure in an autoclave. Since the drive unit can thereby be easily sterilized, the drive unit does not need to be disposed of after each treatment and instead can be reused for further cataract treatments. Since the injector is arranged in the channel, it is advantageously secured against slipping radially with respect to the longitudinal axis of the injector. By providing the drive unit with the motor, it is possible to rotate the second coupling half at a particularly uniform speed, as a result of which the translational movement of the plunger also takes place at a particularly uniform speed. The intraocular lens thereby moves in the cannula at the particularly uniform speed, as a result of which sticking and slipping of the intraocular lens, and possibly associated damage to the intraocular lens, is less likely.

It is preferred that the drive unit is a reusable component and the injector has a disposable component. The entire injector here may be a disposable component. Alternatively, it is conceivable for the second coupling half to be a reusable component that can also be sterilized, and for the remaining part of the injector to be a disposable component.

The first coupling half is preferably mounted in a sliding manner on the annular housing portion. This is advantageously a form of mounting which is simple and inexpensive. In addition, the annular housing portion carries out a dual function by firstly forming part of the housing and therefore helping to encapsulate the first coupling half, and thus allowing the drive unit to be sterilized, and secondly acting as a bearing for the first coupling half. In order to support the first coupling half in a sliding manner on the annular housing portion, the first coupling half can have a non-magnetic sliding ring which is configured to slide on the annular housing portion. As an alternative to the non-magnetic sliding ring, it is conceivable for the first coupling half to have a plurality of non-magnetic sliding ring portions which are spaced apart from one another in the circumferential direction and are configured to slide on the annular housing portion.

Alternatively, it is conceivable for a non-magnetic ball bearing to be provided, by means of which the first coupling half is mounted on the annular housing portion.

According to the invention, the first coupling half has at least one permanent magnet and the second coupling half has a soft magnetic material. It is preferred that the second coupling half is composed of the soft magnetic material. The permanent magnet magnetizes the soft magnetic material and is thus capable of driving the second coupling half into the second rotational movement. The soft magnetic material is less expensive than it would be if permanent magnets were to be provided in the second coupling half.

The first coupling half preferably has an annular permanent magnet holder and a plurality of permanent magnets which are fastened to the permanent magnet holder at a distance from one another in the circumferential direction of the permanent magnet holder. It is particularly preferred here that the permanent magnets are arranged uniformly along the entire circumference of the permanent magnet holder.

It is preferred that the second coupling half has a ring and a plurality of projections protruding outward from the ring radially with respect to the ring, wherein each of the projections is assigned to precisely one of the permanent magnets. As a result, magnetic polarization is generated in each of the projections. The magnetic polarization in each of the projections leads to the coupling between the first coupling half and the second coupling half being relatively strong, as a result of which a relatively large force can be transmitted from the first coupling half to the second coupling half for driving the second coupling half without the second coupling half unintentionally moving past the first coupling half.

The permanent magnets are preferably polarized in the radial direction with respect to the permanent magnet holder. A particularly strong magnetic field is thereby applied to the projections, as a result of which the coupling between the first coupling half and the second coupling half is particularly strong.

The permanent magnets are preferably polarized in each case in an alternating manner to one another in opposite directions along the circumference of the ring. The magnetic field lines of two adjacent permanent magnets thus mutually reinforce each other, as a result of which the coupling between the first coupling half and the second coupling half is very particularly strong.

It is preferred that the permanent magnets each have a concave surface facing inward radially with respect to the permanent magnet holder, said surface being configured to slide on the annular housing portion, such that the first coupling half is mounted in a sliding manner on the annular housing portion. Since it is the permanent magnets, and not also the permanent magnet holder, which slide on the annular housing portion, the frictional resistance during the first rotational movement is comparatively low. It is conceivable for the first coupling half to have a non-magnetic coating that is applied to the concave surfaces. The effect achieved by this is that the permanent magnets do not slide directly on the annular housing portion. Alternatively, it is conceivable for the permanent magnets to be formed from permanent magnetic particles and from a plastics matrix into which the permanent magnetic particles are introduced.

The drive unit preferably has a fastening means which is configured to fasten the injector such that it does not rotate. This makes it possible to prevent the injector from rotating during the second rotational movement. Particularly preferably, the fastening means fastens the injector at a part of the injector that is different from another part of the injector on which the second coupling half acts.

The invention is explained in more detail below with reference to the appended schematic drawings.

Figure 1:
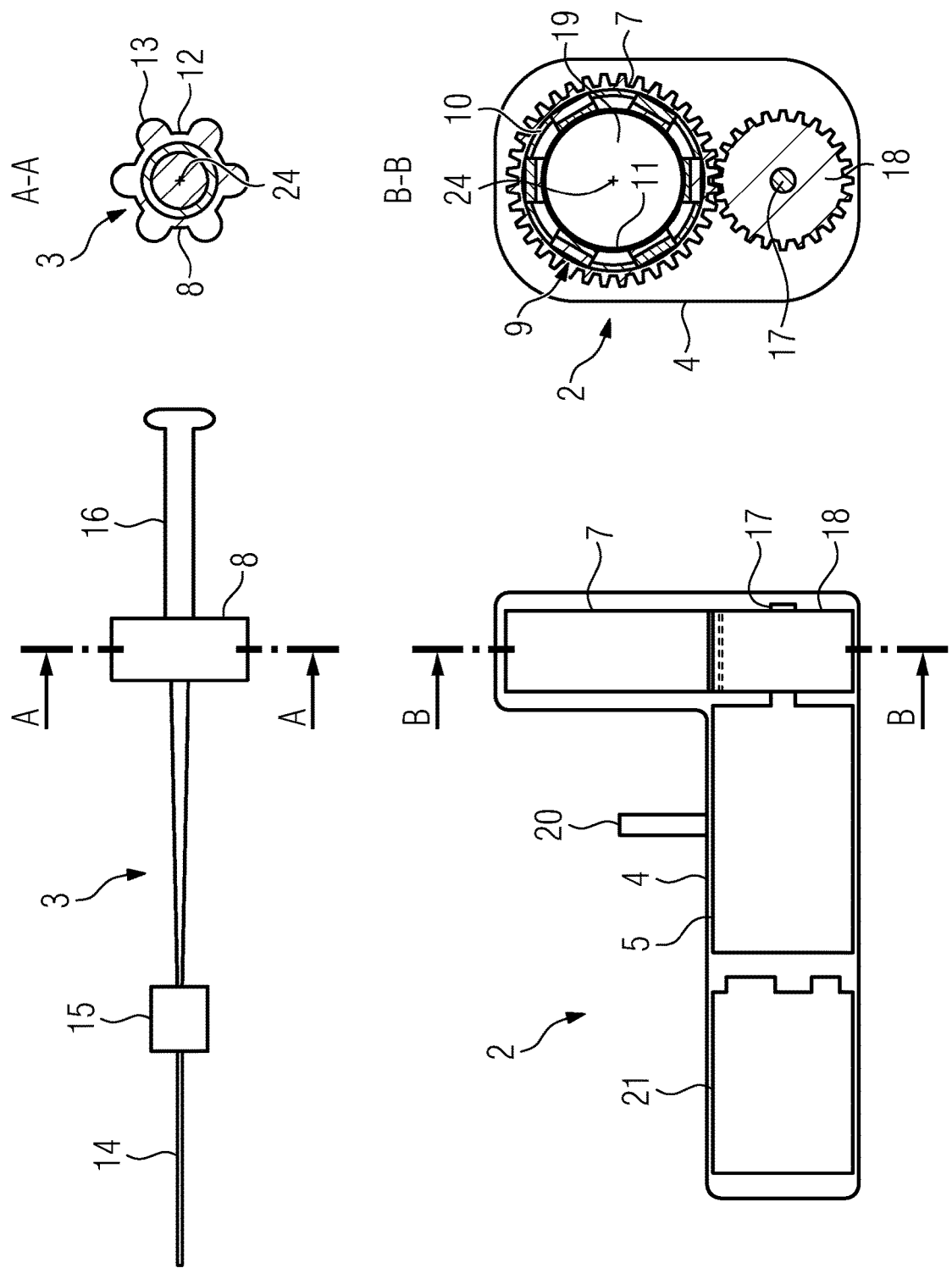
FIG. 1 shows a schematic representation of a preferred embodiment of the injector assembly according to the invention in different sections, wherein an injector of the injector assembly is arranged outside a drive unit of the injector assembly for the purpose of illustration.
Figure 2:
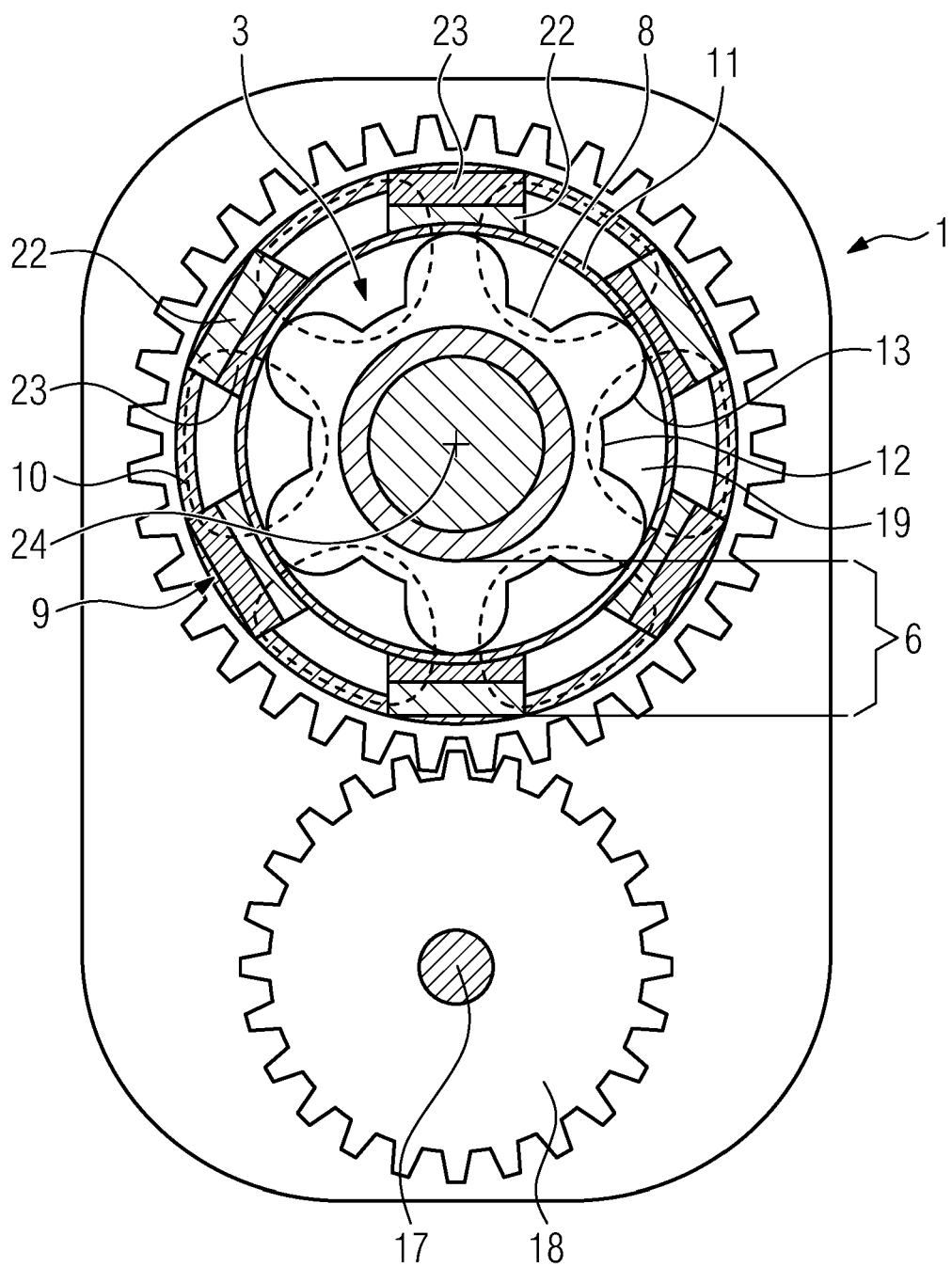
FIG. 2 shows the sections A-A and B-B from FIG. 1 of the injector assembly, wherein the injector is mounted on the drive unit.

As can be seen from FIGS. 1 and 2, an injector assembly 1 has an injector 3, a drive unit 2 and a magnetic coupling 6. The injector 3 has an intraocular lens, a plunger and a cannula 14 and is configured to move the intraocular lens through the cannula 14 by means of a translational movement of the plunger. The drive unit 2 has a first coupling half 7 of the magnetic coupling 6, a motor 5 and a housing 4, within which the first coupling half 7 and the motor 5 are encapsulated. The motor 5 is configured to drive the first coupling half 7 into a first rotational movement. The housing 4 has an annular housing portion 11 which delimits a channel 19 which has a circular cross section. The injector 3 has a second coupling half 8 of the magnetic coupling 6, wherein the injector 3 and the second coupling half 8 are arranged in the channel 19. The first coupling half 7 is arranged around the annular housing portion 11 and is thus configured to carry out the first rotational movement around the annular housing portion 11 and therefore to drive the second coupling half 8 into a second rotational movement by means of a magnetic field of the magnetic coupling 6 penetrating the annular housing portion 11. The injector 3 is configured to convert the second rotational movement into the translational movement of the plunger.

The first rotational movement and the second rotational movement, as illustrated in FIGS. 1 and 2, can be carried out about a common axis of rotation 24, wherein the center point of the circular cross section of the channel 19 lies on the axis of rotation 24.

So that the injector 3 is configured to convert the second rotational movement into the translational movement of the plunger, the injector 3 can have a screw mechanism. To form the screw thread, the injector 3 can, for example, as FIG. 1 shows, have a barrel 16 within which the plunger is arranged. The barrel 16 has the internal thread and the plunger has the external thread, wherein the internal thread and the external thread are in engagement with each another. The second coupling half 8 can be in engagement with the plunger, such that the second rotational movement is also transmitted to the plunger, as a result of which the translational movement of the plunger is generated.

As FIG. 1 also shows, the housing 4 can completely encapsulate all the components of the drive unit 2. In the event that the drive unit 2 has a power supply 21, for example a battery, which is configured to supply the motor 5 with power, the power supply 21 is also encapsulated in the housing 4. The drive unit 2 can also have other components, such as, for example, transmitting units and/or receiving units, which are configured to control the motor 5. The other components can also be encapsulated by the housing 4.

As can be seen from FIG. 1, the injector 3 can have a chamber 15 in which the intraocular lens is introduced. In this case, the plunger is configured first to move the intraocular lens into the cannula 14 and then to move it out of the end of the cannula 14 facing away from the chamber 15. The chamber 14 can have a cross-sectional tapering, such that the intraocular lens is folded during the translational movement before it reaches the cannula 14.

It is conceivable for the drive unit 2 to be a reusable component and the injector 3 to have a disposable component. The entire injector 3 here can be a disposable component. Alternatively, it is conceivable for the second coupling half 8 to be a reusable component that can also be sterilized, and for the remaining part of the injector 3 to be a disposable component. In the event that the second coupling half 8 is the reusable component, a force-fitting and/or form-fitting connection can be provided between the second coupling half 8 and the plunger.

FIGS. 1 and 2 show that the first coupling half 7 has an annular permanent magnet holder 10 and a plurality of permanent magnets 9 which are fastened to the permanent magnet holder 10 at a distance from one another in the circumferential direction of the permanent magnet holder 10.

The permanent magnets 9 are fastened to the inner surface of the permanent magnet holder 10 and thus protrude inward from the permanent magnet holder 10 radially with respect to the permanent magnet holder 10. In particular, an even number of permanent magnets 9 is provided, which are distributed uniformly along the entire circumference of the permanent magnet holder 10. The permanent magnets 9 are polarized in the radial direction with respect to the permanent magnet holder 10, wherein the permanent magnets 9 are polarized in each case in an alternating manner to one another in opposite directions along the circumference of the ring 12. This is achieved in that, as illustrated in FIGS. 1 and 2, in a first group of permanent magnets 9, which has one half of the permanent magnets 9, a north pole 22 of the permanent magnet 9 is arranged facing away from the permanent magnet holder 10 and a south pole 23 of the permanent magnet 9 is arranged facing the permanent magnet holder 10. In a second group of permanent magnets 9, which has the other half of the permanent magnets 9, a south pole 23 of the permanent magnet 9 is arranged facing away from the permanent magnet holder 10 and a north pole 22 of the permanent magnet 9 is arranged facing the permanent magnet holder 10. Each of the permanent magnets 9 from the second group is adjacent here to two of the permanent magnets 9 from the first group.

The second coupling half 8 can have a ring 12 and a plurality of projections 13 protruding outward from the ring 12 radially with respect to the ring 12. The projections 13 are arranged distributed uniformly along the circumference of the ring 12 and the number of projections 13 is equal to the number of permanent magnets 9, such that each of the projections 13 is assigned to precisely one of the permanent magnets 9. The second coupling half 8 can have a soft magnetic material or can be composed of the soft magnetic material. In particular, the projections 13 and the ring 12 can have a soft magnetic material or can be composed of the soft magnetic material. In particular, the second coupling half 8 has no permanent magnet. The dashed lines in FIG. 2 represent the magnetic field lines of the magnetic field of the magnetic coupling 6. It can be clearly seen that the magnetic field lines of two adjacent permanent magnets 9 are always reinforced.

As can be seen from FIGS. 1 and 2, the permanent magnets 9 can each have a concave surface facing inward radially with respect to the permanent magnet holder 10, said surface being configured to slide on the annular housing portion 11, such that the first coupling half 7 is mounted in a sliding manner on the annular housing portion 11. The radius of curvature of the concave surface can be identical here to the radius of curvature of that surface of the annular housing portion 11 which is in contact with the concave surface of the permanent magnets 9.

FIG. 1 shows that the drive unit can have a fastening means 20 which is configured to fasten the injector 3 such that it does not rotate. The fastening means 20 here can fasten the injector 3 at a part of the injector 3 that is different from the plunger. The fastening means 20 can be, for example, a clip that protrudes from the housing 4.

As can be seen from FIG. 1, the housing 4 can have a housing part which protrudes from the remaining housing 4 and has the annular housing portion 11. The motor 5 is arranged in the remaining part of the housing 4. In the event that the drive unit 2 has the power supply 21, the power supply 21 can also be arranged in the remaining part of the housing 4. The motor 5 has a shaft 17 driven by the motor 5 and the drive unit 2 has a driving gear wheel 18 which is fastened to the shaft 17, is at least partially arranged in the remaining part of the housing 4 and is driven by the shaft 17. The outer side of the permanent magnet holder 10 is designed as a gear wheel that engages in the driving gear wheel 18 such that the motor 5 is configured to drive the second coupling half 8 via the shaft 17, via the driving gear wheel 18 and the first coupling half 7. In the event that the fastening means 20 is provided, it can protrude from the housing 4 in the same direction as the housing part that protrudes from the remaining housing 4.

The drive unit 2 can have a switch which is mounted on the outside of the housing 4 and is configured such that its actuation enables it to control the motor 5. Alternatively, it is conceivable for the injector assembly to have a remote switch which is configured such that its actuation enables it to control the motor 5 remotely. For example, the remote switch can be a foot pedal.

LIST OF REFERENCE SIGNS 1 injector assembly
2 drive unit
3 injector
4 housing
5 motor
6 magnetic coupling
7 first coupling half
8 second coupling half
9 permanent magnet
10 annular permanent magnet holder
11 annular housing portion
12 ring
13 projection
14 cannula
15 chamber
16 barrel
17 shaft
18 driving gear wheel
19 channel
20 fastening means
21 power supply
22 north pole
23 south pole
24 axis of rotation

The invention claimed is:

1. An injector assembly with an injector, which has a plunger and a cannula and is configured to move an intraocular lens through the cannula by means of a translational movement of the plunger, a magnetic coupling and a drive unit, which has a first coupling half of the magnetic coupling, a motor, which is configured to drive the first coupling half into a first rotational movement, and a housing, within which the first coupling half and the motor are encapsulated and which has an annular housing portion which delimits a channel which has a circular cross section, wherein the injector has a second coupling half of the magnetic coupling, and the injector and the second coupling half are arranged in the channel, wherein the first coupling half is arranged around the annular housing portion and is thus configured to carry out the first rotational movement around the annular housing portion and therefore to drive the second coupling half into a second rotational movement by means of a magnetic field of the magnetic coupling penetrating the annular housing portion, wherein the injector is configured to convert the second rotational movement into the translational movement of the plunger, wherein the first coupling half has at least one permanent magnet and the second coupling half has a soft magnetic material.

2. The injector assembly as claimed in claim 1, wherein the drive unit is a reusable component and the injector has a disposable component.

3. The injector assembly as claimed in claim 1, wherein the first coupling half is mounted in a sliding manner on the annular housing portion.

4. The injector assembly as claimed in claim 1,
wherein the first coupling half has an annular permanent magnet holder and a plurality of permanent magnets which are fastened to the permanent magnet holder at a distance from one another in the circumferential direction of the permanent magnet holder.

5. The injector assembly as claimed in claim 4, wherein the second coupling half has a ring and a plurality of projections protruding outward from the ring radially with respect to the ring, wherein each of the projections is assigned to precisely one of the permanent magnets.

6. The injector assembly as claimed in claim 5, wherein the permanent magnets are polarized in the radial direction with respect to the permanent magnet holder.

7. The injector assembly as claimed in claim 6, wherein the permanent magnets are polarized in each case in an alternating manner to one another in opposite directions along the circumference of the ring.

8. The injector assembly as claimed in claim 4, wherein the permanent magnets each have a concave surface facing inward radially with respect to the permanent magnet holder, said concave surface being configured to slide on the annular housing portion, such that the first coupling half is mounted in a sliding manner on the annular housing portion.

9. The injector assembly as claimed in claim 4, wherein the permanent magnets are polarized in the radial direction with respect to the permanent magnet holder.

10. The injector assembly as claimed in claim 1, wherein the drive unit has a fastening means which is configured to fasten the injector such that it does not rotate.

* * * * *